(12) United States Patent
Liu

(10) Patent No.: US 9,694,210 B2
(45) Date of Patent: Jul. 4, 2017

(54) MULTI-PURPOSE RADIATION THERAPY SYSTEM

(71) Applicant: Xi'an Cyber Medical Technology Co., Ltd., Xi'an (CN)

(72) Inventor: Haifeng Liu, Xi'an (CN)

(73) Assignee: CYBERMED TECHNOLOGIES (XI'AN) CO., LTD., Xi'An (CN)

( * ) Notice: Subject to any disclaimer, the term of this patent is extended or adjusted under 35 U.S.C. 154(b) by 0 days.

(21) Appl. No.: 15/350,143

(22) Filed: Nov. 14, 2016

(65) Prior Publication Data

US 2017/0065833 A1    Mar. 9, 2017

Related U.S. Application Data

(63) Continuation of application No. 14/437,333, filed on Apr. 21, 2015, now Pat. No. 9,526,919.

(51) Int. Cl.
*A61N 5/01* (2006.01)
*A61N 5/10* (2006.01)
*A61B 6/02* (2006.01)

(52) U.S. Cl.
CPC ............ *A61N 5/1082* (2013.01); *A61B 6/022* (2013.01); *A61N 5/1045* (2013.01); *A61N 5/1047* (2013.01); *A61N 5/1049* (2013.01); *A61N 5/1064* (2013.01); *A61N 5/1084* (2013.01); *A61N 2005/1061* (2013.01)

(58) Field of Classification Search
CPC ...... A61N 5/1084; A61N 5/1081; A61N 5/01; A61N 5/10; A61N 5/1065; A61N 5/1077; A61N 5/1082; G21K 1/046

USPC ........ 378/65, 207, 63, 64; 250/341.7, 494.1, 250/505.1; 600/427

See application file for complete search history.

(56) References Cited

U.S. PATENT DOCUMENTS

| | | | | |
|---|---|---|---|---|
| 5,537,452 A * | 7/1996 | Shepherd | ............... | A61N 5/103 378/148 |
| 7,831,013 B2 * | 11/2010 | Star-Lack | .............. | A61B 6/025 378/23 |
| 8,139,714 B1 * | 3/2012 | Sahadevan | ............. | A61N 5/025 378/63 |
| 8,173,983 B1 * | 5/2012 | Sahadevan | ........... | A61N 5/1084 250/341.7 |
| 8,254,521 B2 * | 8/2012 | Brooks | .................. | A61B 6/502 378/37 |
| 8,300,766 B2 * | 10/2012 | Handa | .................... | A61B 6/022 378/207 |
| 8,637,841 B2 * | 1/2014 | Prince | .................. | A61N 5/1045 250/492.1 |
| 8,682,414 B2 * | 3/2014 | Nishimoto | ............. | A61N 5/103 378/62 |
| 8,712,011 B2 * | 4/2014 | Robar | .................. | A61N 5/1049 378/62 |

(Continued)

*Primary Examiner* — David A Vanore
(74) *Attorney, Agent, or Firm* — Hemisphere Law, PLLC

(57) ABSTRACT

The present invention relates to a multi-purpose radiation therapy system. The radiation therapy system comprises a base, a treatment couch, a rotatable gantry, and at least two radiotherapeutic apparatuses. The treatment couch and the rotatable gantry are arranged on the base. The at least two radiotherapeutic apparatuses include at least one focused radiotherapeutic unit with multi-source and at least one intensity modulated radiotherapeutic unit, and are together installed on the rotatable gantry movably.

20 Claims, 2 Drawing Sheets

(56) References Cited

U.S. PATENT DOCUMENTS

| | | | | |
|---|---|---|---|---|
| 9,044,604 B2* | 6/2015 | Dirauf | ............... | A61B 6/032 |
| 9,082,520 B2* | 7/2015 | Prince | ............... | A61N 5/1045 |
| 9,149,654 B2* | 10/2015 | Handa | ............... | A61N 5/1049 |
| 9,149,656 B2* | 10/2015 | Tanabe | ............... | A61N 5/1067 |
| 9,155,910 B1* | 10/2015 | Sahadevan | ............... | A61N 5/1077 |
| 9,283,403 B2* | 3/2016 | Mazin | ............... | A61B 6/037 |
| 2012/0307973 A1* | 12/2012 | Dirauf | ............... | A61B 6/032 |
| | | | | 378/62 |
| 2014/0321615 A1* | 10/2014 | Carlsson | ............... | A61N 5/1049 |
| | | | | 378/62 |
| 2015/0251022 A1* | 9/2015 | Liu | ............... | A61N 5/1081 |
| | | | | 600/1 |
| 2016/0166215 A1* | 6/2016 | Mazin | ............... | A61B 6/037 |
| | | | | 250/363.03 |
| 2016/0220848 A1* | 8/2016 | Adler, Jr. | ............... | A61N 5/1082 |

\* cited by examiner

MULTI-PURPOSE RADIATION THERAPY SYSTEM

CROSS-REFERENCE TO RELATED APPLICATION

This application is a continuation of U.S. application Ser. No. 14/437,333, filed on Apr. 21, 2015, which is hereby incorporated by reference herein.

TECHNICAL FIELD

The present disclosure relates to the technical field of radiotherapy treatment system, and in particular, to a multi-purpose radiation therapy system.

BACKGROUND

Medical equipment for radiation therapy treats tumorous tissue with high energy radiation. Two types of radiation therapy methods are generally employed for radiation therapy, namely, stereotaxic multi-source focused radiation therapy method and adaptive intensity modulated radiation therapy (IMRT) method. Regarding the stereotaxic multi-source focused radiation therapy method, a plurality of radioactive emission rays are focused to one focal point (namely, the target region), so that high-dose irradiation is performed on the tumor which is in the target region. This multi-source focused radiation therapy method may be adopted to perform high-dose irradiation for tumor tissues, while radiation damage for surrounding tissues is small. This multi-source focused radiation therapy method, with a precise therapeutic property, has a very good therapeutic effect for intracranial tumors or head and neck tumors. However, for a body tumor that has a complicated shape or that is large, the foregoing multi-source focused radiation therapy method has its limits, and the conformal knife radiation therapy method is required. The conformal knife radiation therapy method adopts a single radioactive source, which is conformally processed and enables a distribution shape of a radiation dose region to be identical with or the same as the shape of the tumor in three dimensions, thereby avoiding or decreasing irradiation for normal tissues. In addition, the radiation dose in the dose region is uniformly distributed.

Currently, there is no radiation therapy device that can integrate the stereotaxic multi-source focused radiation therapy method with the adaptive intensity modulated radiation therapy method. In other words, the current radiation therapy devices cannot implement both accurate multi-source focused therapy and conformal therapy on one device. For patients, different therapy methods cannot be selected for different tumors or a same tumor on a same device.

DETAILED DESCRIPTION

To make the objective, technical solution, and advantages of the present invention more clear, the following section describes the technical solution of the present invention in combination with the accompanying drawings. It should be understood that the embodiment described here is only exemplary one for illustrating the present invention, and is not intended to limit the present invention.

Figure 1:
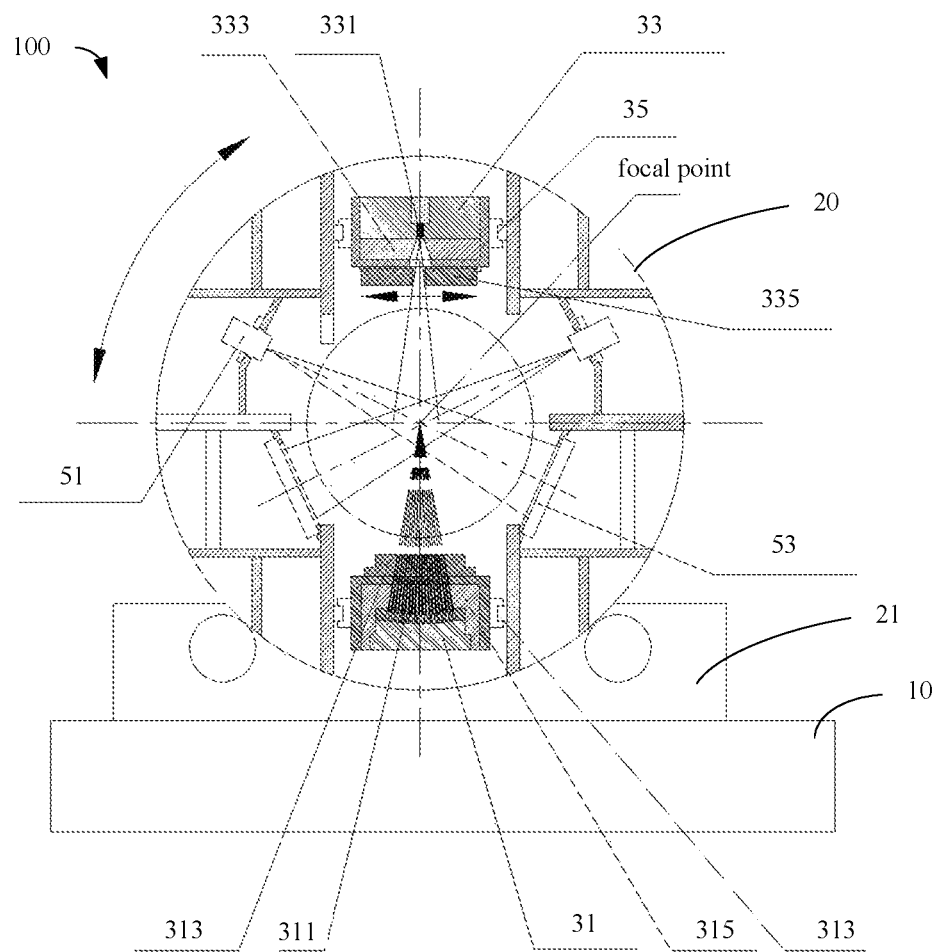
FIG. 1 is a schematic diagram of a multi-purpose radiation therapy system according to an embodiment of the present invention.
Figure 2:
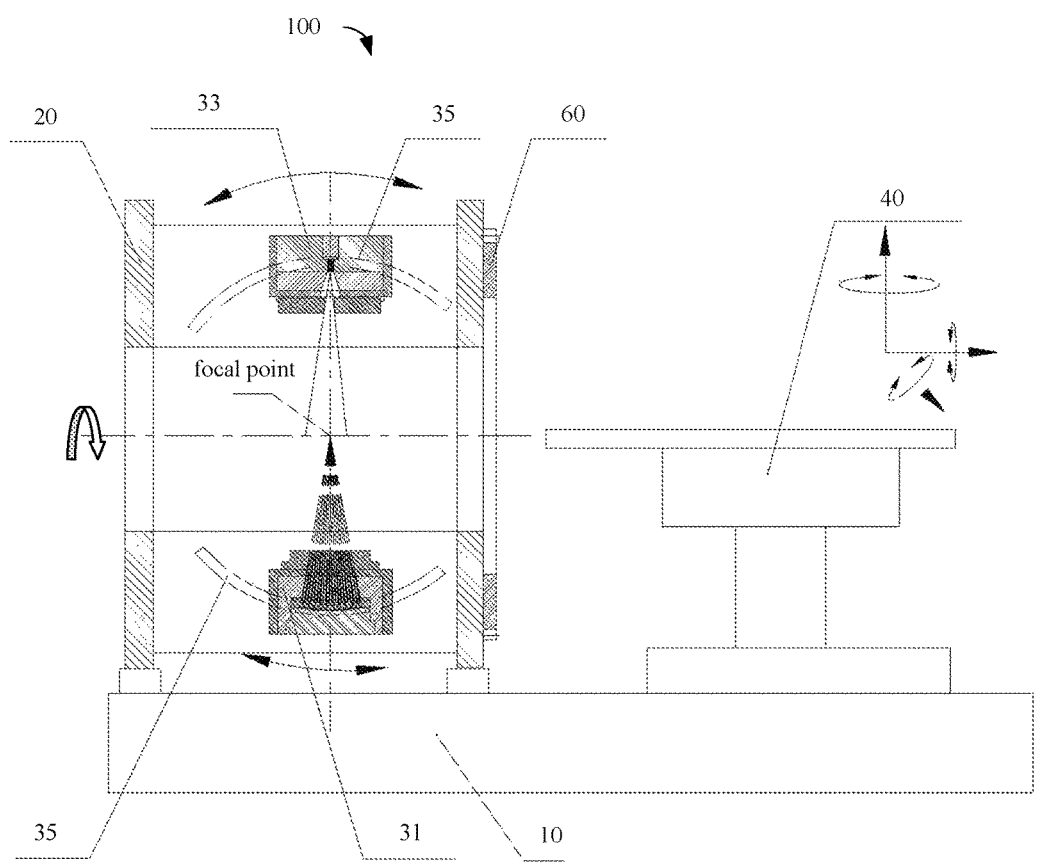
FIG. 2 is a side view of the multi-purpose radiation therapy system according to the embodiment of the present invention.

For a better understanding of the technical solution of the present invention, the applicant describes a multi-purpose radiation therapy system of the embodiment of the present invention by using detailed implementation manners of FIG. 1 and FIG. 2. FIG. 1 is a schematic diagram of a radiation therapy system 100 that integrates stereotaxic multi-source focused radiation therapy structure with adaptive intensity modulated radiation therapy structure according to an embodiment of the present invention. As shown in FIG. 1, the radiation therapy system 100 includes a base 10, a rotatable gantry 20, a radiotherapeutic apparatus, and a treatment couch 40. The base 10 supports the whole radiation therapy system 100 support. The treatment couch 40 is arranged on the base 10, and is movably connected to the base 10, e.g. by using screws and pins. The treatment couch 40 is used to support and position a patient, and can accurately deliver the patient to a specified position for treatment. The treatment couch 40 is further sleeved in the rotatable gantry 20. The rotatable gantry 20 is further arranged on the base 10, and is connected to the base 10 by a rolling support 21. The rotatable gantry 20 rotates around an axial line, which is defined as a axis X of the rotatable gantry, by means of, e.g. gear 60 drive.

The radiation therapy system 100 further comprises a core portion, namely, the radiotherapeutic apparatus. In one embodiment of the present invention, the radiotherapeutic apparatus involves two types of radiotherapeutic apparatuses, namely, a focused radiotherapeutic apparatus and an adaptive intensity modulated radiotherapeutic apparatus. More specifically, the radiotherapeutic apparatus includes a focused radiotherapeutic unit 31 and an intensity modulated radiotherapeutic unit 33. The focused radiotherapeutic unit 31 may perform Stereotaxic Radiosurgery (SRS) or Imaging Guide Radiation Therapy (IGRT). The intensity modulated radiotherapeutic unit 33 may perform 3-Dimensional Conformal Radiation Therapy (3D-CRT), or Intensity Modulated Radiation Therapy (IMRT), or Stereotactic Body Radiation Therapy (SBRT), or Imaging Guide Radiation Therapy (IGRT). Specifically, in this embodiment, the focused radiotherapeutic unit 31 is a multi-functional device which integrates the functions of SRS and IGRT. Similarly, the intensity modulated radiotherapeutic unit 33 is a multi-functional device which integrates the functions of 3D-CRT, (IMRT), (SBRT), and (IGRT). When one or more of the mentioned functions is required to be performed, the corresponding function/ability can be selected, by switching the predetermined functions of the focused radiotherapeutic unit 31 and/or the intensity modulated radiotherapeutic unit 33.

The focused radiotherapeutic unit 31 and the intensity modulated radiotherapeutic unit 33 are distributed at both sides of the rotatable gantry axis X. Because the rotatable gantry 20 rotates around the rotatable gantry axis X (i.e. the gyration center), the radiotherapeutic apparatuses are driven to continuously or reciprocally rotate 360 degrees around the rotatable gantry axis X. In addition, the focused radiotherapeutic unit 31 and the intensity modulated radiotherapeutic unit 33 are connected to the rotatable gantry 20 and movable along an axial direction of the rotatable gantry 20, via respective arc-shaped guiding rail 35. Specifically, each arc-shaped guiding rail 35 is attached to the inner sidewall of the rotatable gantry 20. In this embodiment, the arc-shaped guiding rails 35 are fixed to the rotatable gantry 20 by screwing at the middle position of the arc-shaped guiding rails 35. The focused radiotherapeutic unit 31 and the intensity modulated radiotherapeutic unit 33 are movably sleeved on the arc-shaped guiding rails 35, respectively. When a target (e.g. tumor) for treatment has been moved, the focused radiotherapeutic unit 31 and/or the intensity modulated radiotherapeutic unit 33 will be driven to move along the arc-shaped guiding rail 35, to track the movement of the target. In this way, the radiotherapeutic apparatuses may continuously swing around a focal point on a rotatable gantry axial plane, and a swinging angle is in a range of 0 to ±47.5 degrees, so as to implement non-coplanar focused or conformal therapy with different incident angles, thereby carrying out tumor therapy more flexibly and effectively. Further, regarding the placement of the focused radiotherapeutic unit 31 and the intensity modulated radiotherapeutic unit 33, an included angle from the focused radiotherapeutic unit 31 and the intensity modulated radiotherapeutic unit 33 to the axis is continuously adjustable between 30 degrees and 180 degrees. Since the radiotherapeutic apparatus can make a continuous incident angle change of maximum ±47.5 degrees and a central rotation of 360-degree around the center, a treatment incident angle of the system may exceed $2\pi$.

The focused radiotherapeutic unit 31 further includes a plurality of radioactive sources 311, a movable collimator 313, and a precollimator 315. The precollimator 315 and the movable collimator 313 are sequencely arranged on a light emitting path of the plurality of radioactive sources 311. In the embodiment of the present invention, the radioactive sources 311 adopt cobalt-60, to generate gamma rays. The gamma rays generated by the cobalt-60 pass through the precollimator 315 and the movable collimator 313, and are focused on one focal point. As such, a focused field, namely, a high-dose region for therapy, is formed. The movable collimator 313 is provided with a plurality of apertures in different size, and the movable collimator 313 is moved while aligning with the radioactive sources 311. The movement of the movable collimator 313 is performed to switch the apertures, so as to change a size and a shape of the focused field. As such, the focused radiotherapeutic unit 31 can be used to implement accurate therapy with a small field size and a high dose.

The intensity modulated radiotherapeutic unit 33 includes a radioactive source 331, a precollimator 333, and a multi-leaf collimator 335. In the embodiment of the present invention, the radioactive source 331 may be a single cobalt source or an X ray generator having an intensity greater than 4 mV. The radioactive source 331 cooperates with the multi-leaf collimator 335 to implement different field shapes on a treatment plane, so as to implement three-dimensional adaptive intensity modulated irradiation. The multi-leaf collimator 335 is implemented with generally used technology, and details will not be described in the embodiment of the present invention.

In addition, the radiation therapy system 100 of the present invention further includes a dynamic image guide system (IGS). In this embodiment, the dynamic image guide system (IGS) is stereo imaging apparatus, and one or two sets/groups of stereo imaging apparatus are assembled on the rotating rotatable gantry 20, and focus to the same focal point of the focused radiotherapeutic unit 31 and the intensity modulated radiotherapeutic unit 33. Generally, each set of the stereo imaging apparatus includes an X-ray generator 51 and an image detection and acquisition system 53. Accordingly, one or two sets of X-ray X-ray generator 51 are installed on the rotatable gantry 20, to perform real-time detection of a body position and/or a spatial position of a target tissue. In this embodiment, two dynamic image guide systems (IGS) are employed, each positioned on a space between the focused radiotherapeutic unit 31 and the intensity modulated radiotherapeutic unit 33. More specifically, the X-ray generator 51 of the dynamic image guide systems (IGS) is structured beside the intensity modulated radiotherapeutic unit 33, while the image detection and acquisition system 53 is structured beside the dynamic image guide systems (IGS). A fixed angle is formed between the two sets of dynamic image guide systems (IGS). In this embodiment, an included angle of the two sets of dynamic image guide systems (IGS) is in a range of 20 degrees to 160 degrees. As a result, space position compensation is performed for the treatment couch 40 and the radiotherapeutic apparatuses according to a detection result, so as to ensure high-precision orientation during treatment and implement accurate radiation therapy.

In the embodiment of the present invention, the focused radiotherapeutic unit 31 and the intensity modulated radiotherapeutic unit 33 are integrated into one radiation therapy system 100, which has a great advantage for some special tumor focuses where two manners of multi-source focused and intensity modulation are required simultaneously or separately for treatment. In the radiation therapy system 100, the intensity modulated radiotherapeutic unit 33 and the focused radiotherapeutic unit 31 may be simultaneously or separately used for irradiation therapy with one positioning, to implement two types of combined radiation therapy, errors caused by multiple times of positioning are reduced, and radiation therapy precision and speed are improved, thereby improving quality and efficiency.

The above descriptions are merely a preferred embodiment of the present invention, but are not intended to limit the present invention. Any modification, equivalent replacement, or improvement made without departing from the spirit and principle of the present invention should fall within the protection scope of the present invention.

What is claimed is:

1. A multi-purpose radiation therapy system, comprising a rotatable gantry and at least two radiotherapeutic apparatuses movably structured to the rotatable gantry, wherein the at least two radiotherapeutic apparatuses comprise at least one focused radiotherapeutic unit with multi-source and at least one intensity modulated radiotherapeutic unit.

2. The multi-purpose radiation therapy system according to claim 1, wherein the at least two radiotherapeutic apparatuses comprise one focused radiotherapeutic unit with multi-source and one intensity modulated radiotherapeutic unit being capable to move in asynchronous way.

3. The multi-purpose radiation therapy system according to claim 1, wherein an angle from the focused radiotherapeutic unit to the intensity modulated radiotherapeutic unit relative to the axis center of the rotatable gantry is between 30 degrees and 180 degrees.

4. The multi-purpose radiation therapy system according to claim 3, wherein an angle from the focused radiotherapeutic unit to the intensity modulated radiotherapeutic unit relative to the axis center of the rotatable gantry is equal to 90 degrees or 180 degrees.

5. The multi-purpose radiation therapy system according to claim 1, wherein the focused radiotherapeutic unit and/or the intensity modulated radiotherapeutic unit are continuously translated on an inner surface of the rotatable gantry along an axial direction of the gantry and toward a predetermined target focal point, for performing focused radiation and/or intensity modulated radiation therapy in different plane and angle of incidence.

6. The multi-purpose radiation therapy system according to claim 5, wherein the focused radiotherapeutic unit and/or the intensity modulated radiotherapeutic unit are connected to the rotatable gantry via respective arc-shaped guiding rails, to be translated along the axial direction of the rotatable gantry.

7. The multi-purpose radiation therapy system according to claim 6, wherein an angle of translation movement of the focused radiotherapeutic unit and/or the intensity modulated radiotherapeutic unit is ranged in 0-±47.5 degrees.

8. The multi-purpose radiation therapy system according to claim 1, wherein the rotatable gantry is 360-degree rotatable around the rotatable gantry axis in a continuous or reciprocal manner.

9. The multi-purpose radiation therapy system according to claim 1, further comprising a dynamic image guide system comprising one or two groups of stereo imaging apparatus, for performing real-time detection of a body position or a focus space position of a patient.

10. The multi-purpose radiation therapy system according to claim 9, wherein an angle between the two groups of stereo imaging apparatus is in a range of 20 degrees to 160 degrees.

11. The multi-purpose radiation therapy system according to claim 9, wherein the stereo imaging apparatus comprises an X-ray generator and an image detection and acquisition system.

12. The multi-purpose radiation therapy system according to claim 1, wherein the focused radiotherapeutic apparatus comprises a plurality of radioactive sources, a precollimator, and a movable collimator, emissions from the radioactive sources pass through the precollimator and the movable collimator to focus to a focal point and form a focused field.

13. The multi-purpose radiation therapy system according claim 12, wherein the movable collimator is provided with apertures in different size, and the movable collimator is configured to switch the apertures to change a size and a shape of the focused field.

14. The multi-purpose radiation therapy system according to claim 1, wherein the intensity modulated radiotherapeutic apparatus comprises a radioactive source, a precollimator, and a multi-leaf collimator.

15. The multi-purpose radiation therapy system according to claim 14, wherein the radioactive source of the adaptive intensity modulated radiotherapeutic apparatus is a single cobalt source or an X-ray generator.

16. A multi-purpose radiation therapy system, comprising a base, a treatment couch, a rotatable gantry, and at least two radiotherapeutic apparatuses, the treatment couch and the rotatable gantry being arranged on the base, wherein the at least two radiotherapeutic apparatuses comprise at least one focused radiotherapeutic unit with multi-source and at least one intensity modulated radiotherapeutic unit, and are together installed on the rotatable gantry movably.

17. The multi-purpose radiation therapy system according to claim 16, wherein the treatment couch is arranged on the base and is movably connected to the base by using screws and/or pins.

18. The multi-purpose radiation therapy system according to claim 16, wherein the rotatable gantry is connected to the base with a rolling support which drives the gantry to rotate by gears.

19. The multi-purpose radiation therapy system according to claim 16, wherein the focused radiotherapeutic unit and the intensity modulated radiotherapeutic unit are connected to the rotatable gantry via respective arc-shaped guiding rails, to be translated along an axial direction of the rotatable gantry.

20. The multi-purpose radiation therapy system according to claim 16, further comprising at least one group of stereo imaging apparatus, for performing real-time detection of a position for the patient or a spatial position of a target tissue.

* * * * *